United States Patent
Cao et al.

(10) Patent No.: US 10,799,183 B2
(45) Date of Patent: Oct. 13, 2020

(54) METHODS AND SYSTEMS FOR WHOLE BODY IMAGING

(71) Applicant: General Electric Company, Schenectady, NY (US)

(72) Inventors: Nan Cao, Beijing (CN); Yongchuan Lai, Beijing (CN); Shiyu Li, Beijing (CN); Ting Zhang, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 29 days.

(21) Appl. No.: 16/183,631

(22) Filed: Nov. 7, 2018

(65) Prior Publication Data

US 2020/0138382 A1 May 7, 2020

(51) Int. Cl.
| | |
|---|---|
| *A61B 5/00* | (2006.01) |
| *G01R 33/56* | (2006.01) |
| *G01R 33/54* | (2006.01) |
| *A61B 5/055* | (2006.01) |
| *G06T 7/00* | (2017.01) |
| *G06T 7/73* | (2017.01) |

(52) U.S. Cl.
CPC .......... *A61B 5/7267* (2013.01); *A61B 5/0555* (2013.01); *G01R 33/543* (2013.01); *G01R 33/5608* (2013.01); *G06T 7/0014* (2013.01); *G06T 7/74* (2017.01); *A61B 2576/00* (2013.01); *G06T 2207/10088* (2013.01); *G06T 2207/20081* (2013.01); *G06T 2207/20084* (2013.01); *G06T 2207/20221* (2013.01); *G06T 2207/30012* (2013.01)

(58) Field of Classification Search
CPC . A61B 5/7267; A61B 5/0555; A61B 2576/00; G06T 7/74; G06T 7/0014; G06T 2207/10088; G06T 2207/30012; G06T 2207/20221; G06T 2207/20081; G06T 2207/20084; G01R 33/543; G01R 33/5608
See application file for complete search history.

(56) References Cited

U.S. PATENT DOCUMENTS

| | | | | |
|---|---|---|---|---|
| 6,500,123 | B1 * | 12/2002 | Holloway | A61B 8/08 600/443 |
| 2005/0213849 | A1 * | 9/2005 | Kreang-Arekul | G06T 3/4038 382/284 |
| 2016/0093048 | A1 | 3/2016 | Cheng et al. | |
| 2018/0365512 | A1 * | 12/2018 | Molchanov | G06K 9/4628 |
| 2019/0130578 | A1 * | 5/2019 | Gulsun | G06N 3/0454 |

FOREIGN PATENT DOCUMENTS

| | | |
|---|---|---|
| CN | 104240226 A | 12/2014 |
| CN | 106846380 A | 6/2017 |
| EP | 3246875 A2 | 11/2017 |

OTHER PUBLICATIONS

Adelson, E. et al., "Pyramid methods in image processing," RCA Engineer, vol. 29, No. 6, Nov. 1, 1984, 9 pages.
Lin, T. et al., "Feature Pyramid Networks for Object Detection," Proceedings of the 2017 IEEE Conference on Computer Vision and Pattern Recognition (CVPR), Jul. 21, 2017, Honolulu, Hawaii, 10 pages.

* cited by examiner

Primary Examiner — Akm Zakaria
(74) Attorney, Agent, or Firm — McCoy Russell LLP

(57) ABSTRACT

Various methods and systems are provided for scanning an image subject along a scan axis. The method includes stitching sectional datasets acquired from different anatomical sections of the image subject based on locations of a landmark in the sectional datasets.

19 Claims, 7 Drawing Sheets

METHODS AND SYSTEMS FOR WHOLE BODY IMAGING

FIELD

Embodiments of the subject matter disclosed herein relate to whole body imaging.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field $B_0$. When a human body, or part of a human body, is placed in the magnetic field $B_0$, the nuclear spins associated with the hydrogen nuclei in tissue water become polarized, wherein the magnetic moments associated with these spins become preferentially aligned along the direction of the magnetic field $B_0$, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coils and is transformed into the image using reconstruction algorithms. Different sections of the human body may be imaged by translating the human body relative to the magnetic field $B_0$.

BRIEF DESCRIPTION

In one embodiment, a method comprises performing a first sectional scan on a first anatomical section of an image subject to obtain a first sectional dataset; performing a second sectional scan on a second anatomical section of the image subject to obtain a second sectional dataset; determining, with a trained deep learning network, a first location of a landmark in the first sectional dataset and a second location of the landmark in the second sectional dataset; and stitching the first sectional dataset and the second sectional dataset based on the first location of the landmark and the second location of the landmark. In this way, a constructed image covering a large range of the imagine subject along a scan axis may be obtained. Further, by stitching sectional datasets from different anatomical sections of the image subject based on the landmark location, discontinuity of the landmark at the overlapped region in the constructed image may be avoided.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
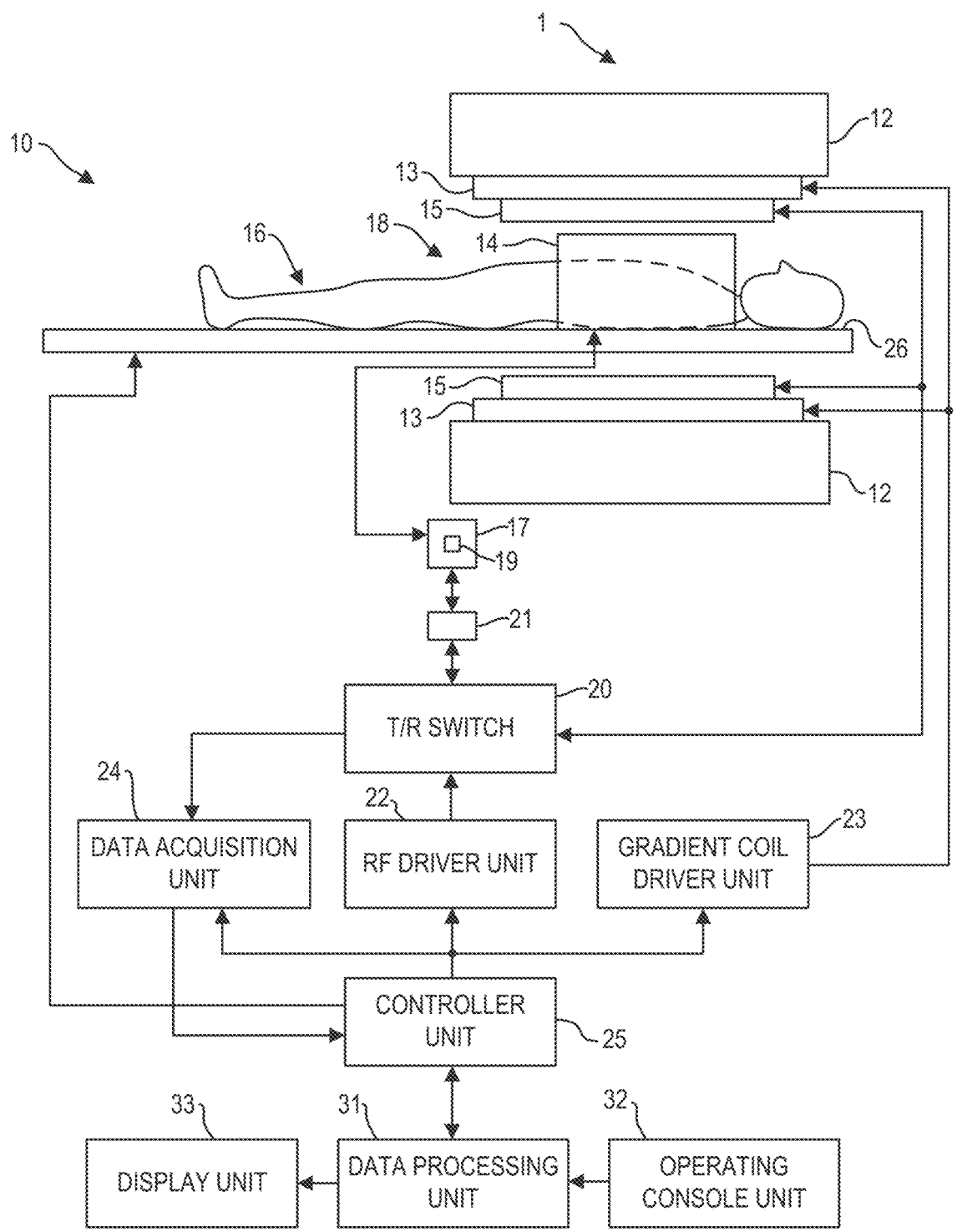
FIG. 1 is a block diagram of an MRI system according to an exemplary embodiment of the invention.

The following description relates to various embodiments of constructing and displaying datasets acquired from different sections of an image subject, i.e., different anatomical stations, via an imaging apparatus, such as the magnetic resonance imaging (MRI) apparatus of FIG. 1. Due to limited scan range of the imaging system, images covering a large section of the subject, such as a whole-body image, cannot be generated via a single scan. In order to address the issue, a plurality of sectional scans of different sections (a.k.a. stations) of the subject may be performed by translating the image subject relative to a scanner of the imaging apparatus along a scan axis. By stitching sectional datasets acquired in the sectional scans together, a constructed image covering a large range along the scan axis may be obtained. In some embodiments, the sectional datasets may be stitched together based on registration of slices in an overlapped region acquired from different sectional scans.

Due to the inhomogeneity of some imaging parameters (such as the distribution of magnetic field strength) across the scan range, stitching artifacts such as discontinuity may appear in the constructed image. For example, a spine may appear broken or misaligned at the stitching location between the two sectional scans. The stitching introduced artifacts may lead to misdiagnosis. For example, the operator may not be able to determine whether or not the discontinuity in the image is caused by the stitching artifacts. As a result, the operator may misinterpret the stitching introduced discontinuity of the spine as spine dislocation.

Figure 2:
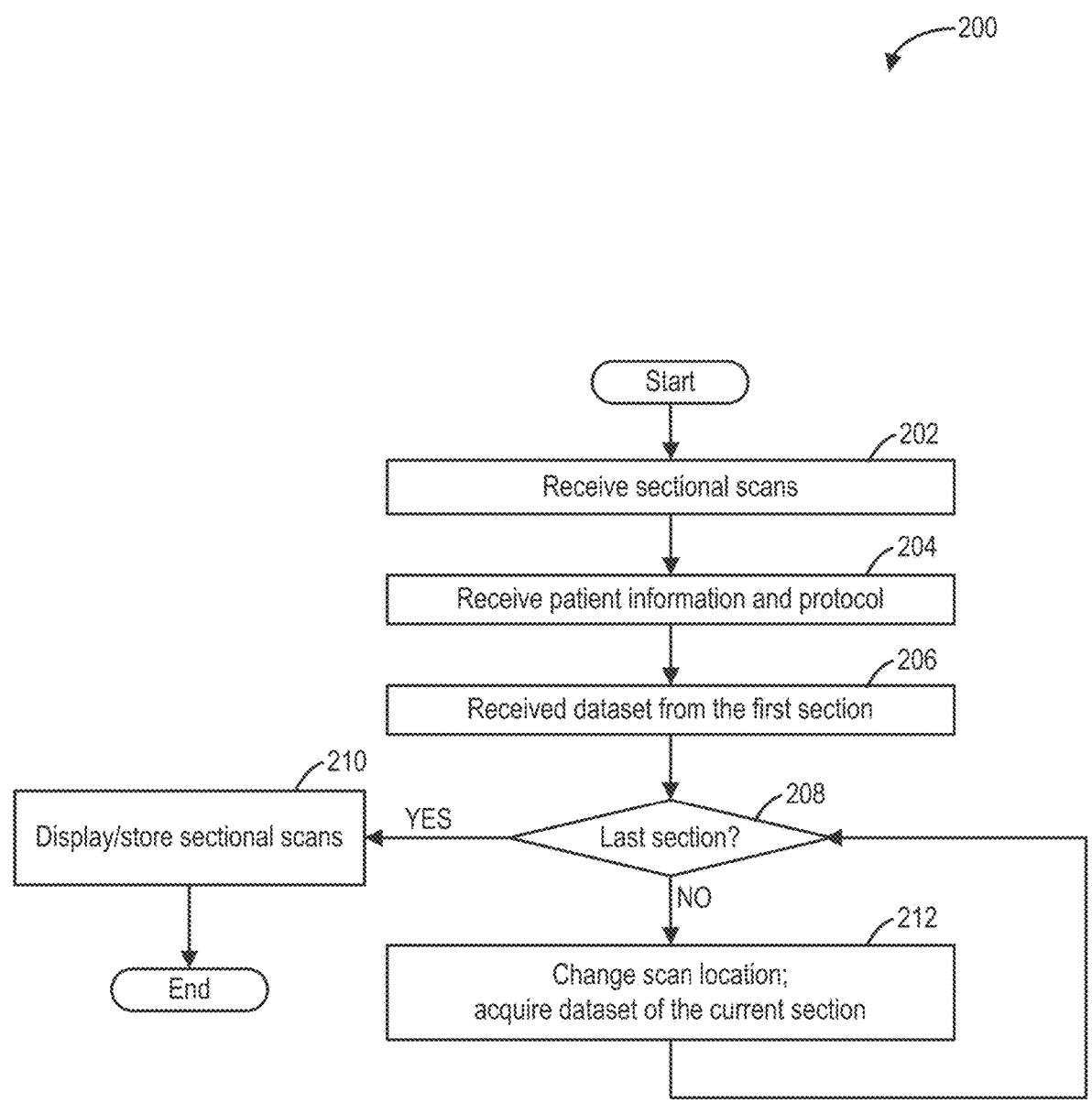
FIG. 2 shows a method for acquiring multiple sectional scans according to an exemplary embodiment.
Figure 3:
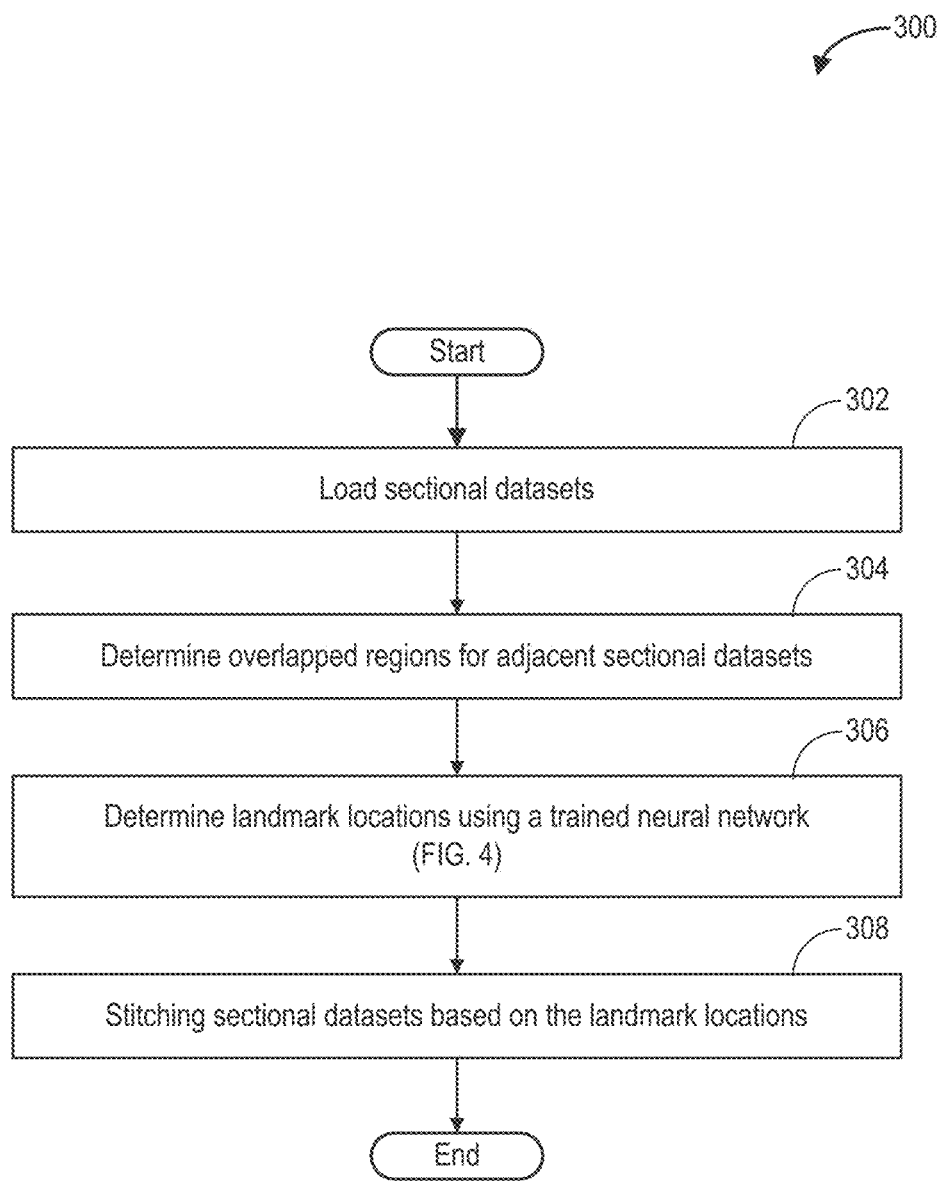
FIG. 3 shows a method of stitching datasets acquired in sectional scans according to an exemplary embodiment.
Figure 5:
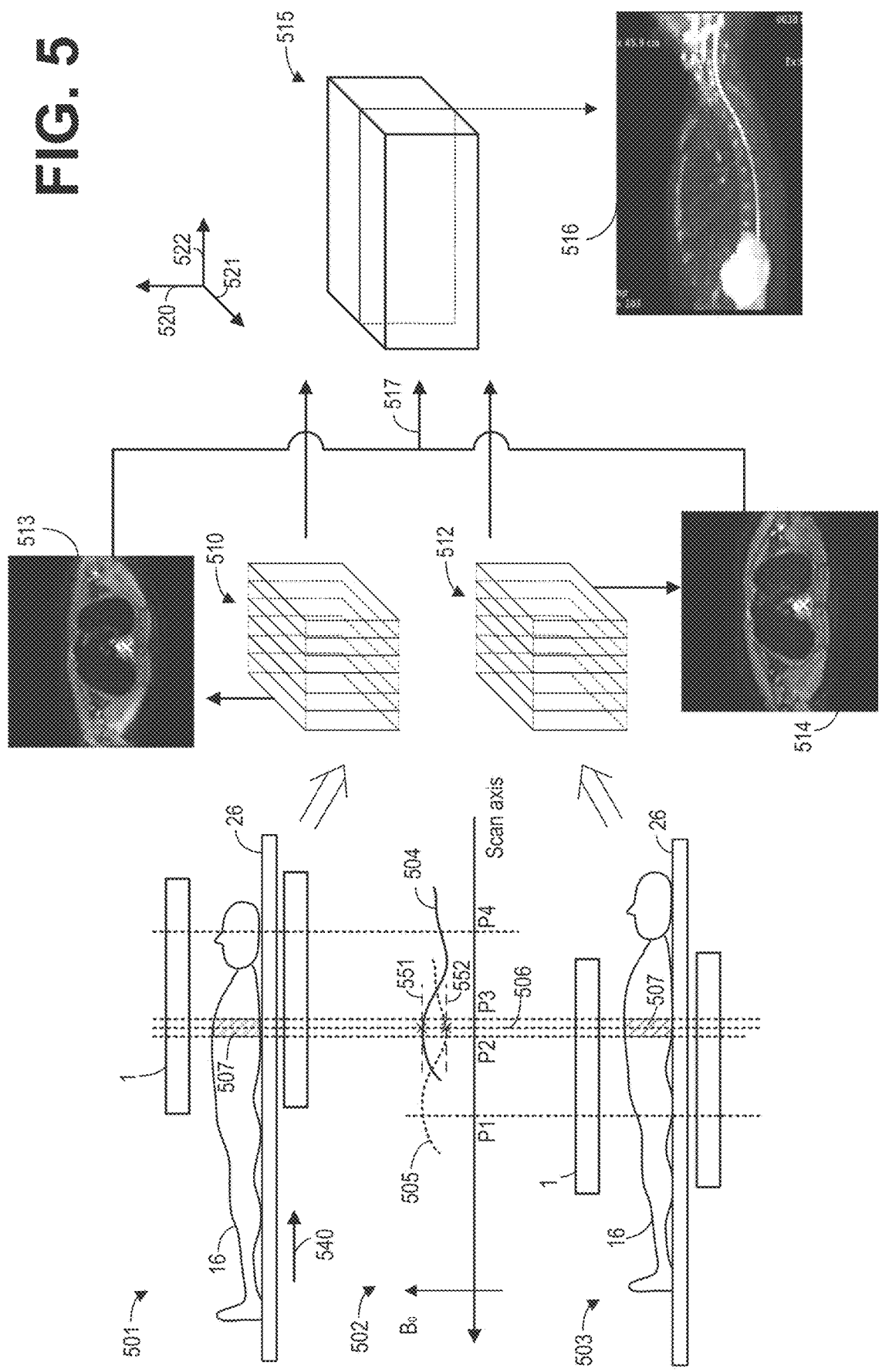
FIG. 5 is a diagram illustrating the implementation of the method of FIG. 3.
Figure 6B:
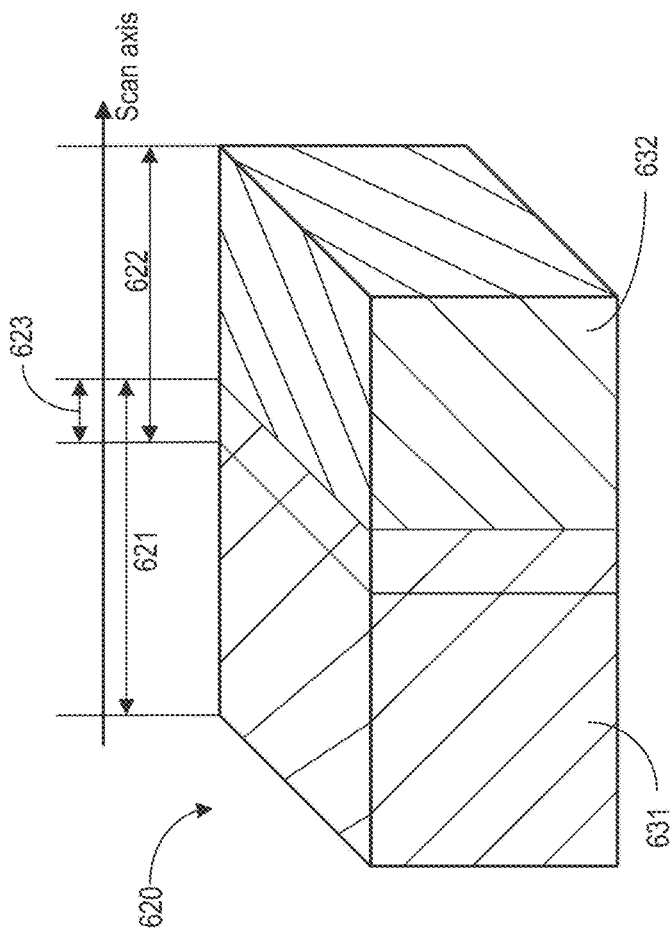
FIG. 6B illustrates a constructed dataset obtained by stitching datasets acquired in sectional scans according to an exemplary embodiment.
Figure 6A:
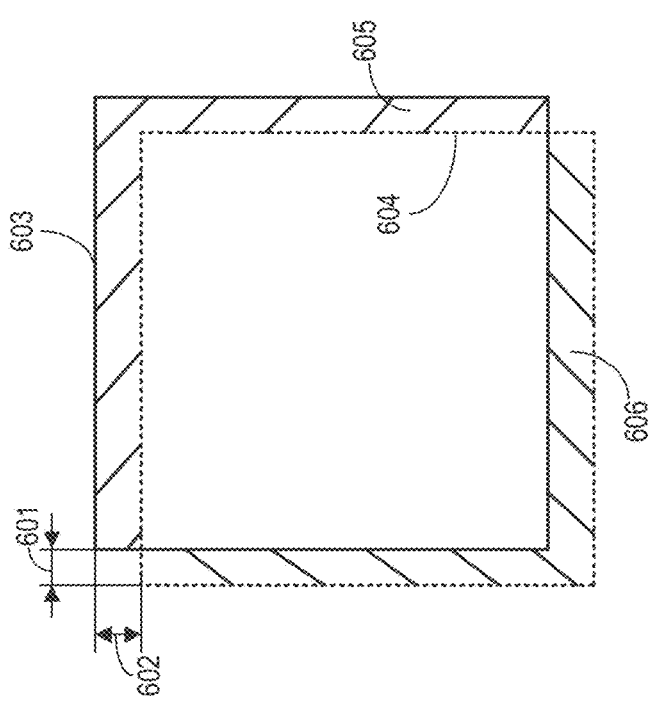
FIG. 6A illustrates shifting an image by an offset.
Figures 7A, 7B:
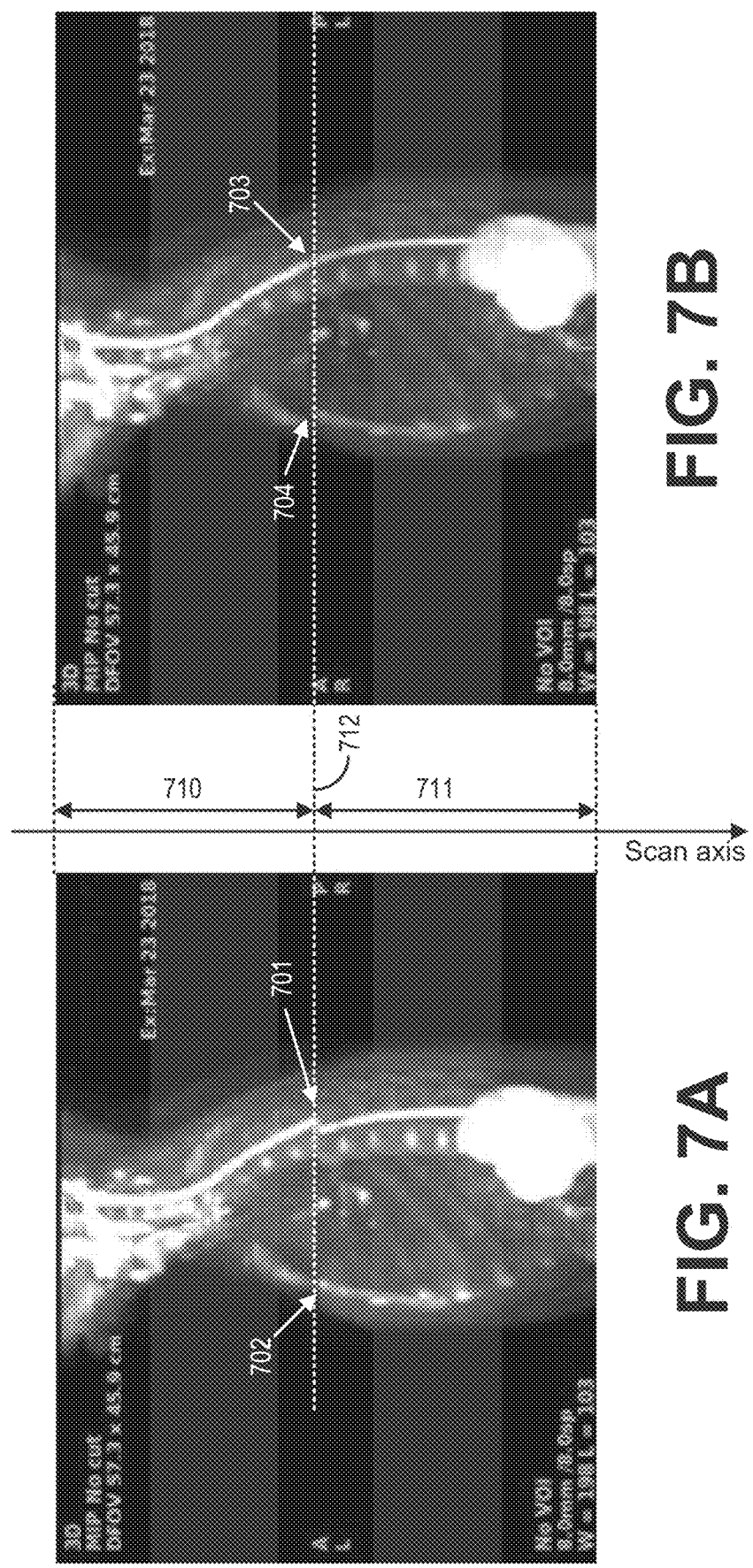
FIG. 7A shows an MR image generated based on constructed datasets obtained using a conventional stitching method.
FIG. 7B shows an MR image generated based on constructed dataset obtained using the stitching method of FIG. 3.

A method for acquiring sectional datasets from multiple sectional scans is shown in FIG. 2. The sectional datasets may be stitched based on an offset of a landmark in adjacent sectional scans as shown in FIG. 3. Locations of the landmark in the sectional scans may be determined via a neural network shown in FIG. 4. The constructed dataset may be obtained by stitching sectional datasets translated by the offset. By stitching the datasets based on localized information in the overlapped region (that is, a subset of data points in the overlapped region) rather than global information (that is, all data points in the overlapped region), the landmark may appear to be continuous in the constructed image. FIG. 5 is a diagram illustrating the implementation of the method of FIG. 3. FIG. 6A illustrates shifting a slice of the sectional dataset by the offset. FIG. 6B illustrates an example of constructed dataset generated from two sectional datasets. FIG. 7A shows an MRI image generated based on constructed datasets obtained using the conventional stitching method. FIG. 7B shows an MRI image generated based on constructed datasets obtained using the method of FIG. 3.

Though a MRI system is described by way of example, it should be understood that the present techniques may also be useful when applied to images acquired using other imaging modalities, such as CT, tomosynthesis, PET, C-arm angiography, and so forth. The present discussion of an MRI imaging modality is provided merely as an example of one suitable imaging modality.

FIG. 1 illustrates a magnetic resonance imaging (MRI) apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

FIG. 2 is a flow chart showing an example method 200 for acquiring sectional datasets from multiple anatomical stations of the image subject. The sectional datasets are obtained by moving a table (such as table 26 of FIG. 1) relative to a scanner (such as scanner 1 of FIG. 1) along a scan axis. Each sectional dataset may be three dimensional and may include a plurality of parallel axial slices (or 2D images) perpendicular to the scan axis. Adjacent sectional datasets may overlap in an overlapped region. In other words, data in the overlapped region is acquired in both of the adjacent sectional scans.

At 202, responsive to the operator's instruction, the table (such as table 26 of FIG. 1) is moved to position the subject (such as a patient) in the imaging space (such as imaging space 18 of FIG. 1).

At 204, operator input is received at the controller regarding the patient information and the imaging protocol. In particular, the operator may select the protocol based on the anatomy to be scanned. The imaging protocol may include a region of interest (ROI) and a field of view (FOV), among other parameters. The FOV may include a range of the scan along a scan axis. Based on the FOV, the number of sectional scans along the scan axis may be determined. Each sectional scan acquires a sectional dataset covering a range along the scan axis. The subject may be translated from one range to another along the scan axis between sectional scans. Adjacent sectional scans may scan an overlapped range along the scan axis.

In some embodiments, the scan axis is the lengthwise axis of the table (such as table 26 of FIG. 1) or the longitudinal axis of the subject. The scan axis may be aligned with the direction of magnetic field $B_0$. In some embodiments, the scan axis may be any appropriate direction determined based on the range of the scan. For example, if the scan range along a particular axis is out of the maximum range defined by the system configuration, the axis may be set as the scan axis, and multiple sectional scans may be performed along the scan axis to cover the full scan range. The maximum range may be determined based on the configuration of the system, such as the range of the RF coil, gradient coil, and the magnetostatic field magnet unit.

The imaging protocol may also include the slice thickness and the number of overlapped slices in the overlapped section of adjacent sectional scans. The overlapped range along the scan axis is the product of the slice thickness and the number of overlapped slices. In some embodiments, the number of overlapped slices is greater than one, so that at least one slice is in the overlapped region.

At 206, the table moves to the starting location of the scan, and the first sectional dataset for the first anatomical section (or station) of the subject is acquired. The sectional dataset may be three dimensional and may include a plurality of parallel slices perpendicular to the scan axis. In some embodiments, each slice is a 2D image (such as a MRI image) reconstructed from k-space data. As such, each sectional dataset includes a series of 2D reconstructed images perpendicular to the scan axis.

At 208, method 200 checks whether the current section is the last section. If the current imaged anatomical section of the subject is the last section, the sectional datasets are displayed and/or stored at 210. In some embodiments, displaying the sectional datasets may include displaying a constructed dataset generated by stitching the sectional datasets using method 300 of FIG. 3. If the current imaged section is not the last section, the next section of the subject is scanned at 212.

At 212, the scan location is changed, and the next section of the subject is scanned. In some embodiments, the scan location is changed by moving the subject along the scan axis. In other embodiments, the subject may be moved along the scan axis by moving the table along the scan axis. In other embodiments, the subject may be moved along the scan axis by moving the scanner along the scan axis. In other embodiments, the subject may be moved along the scan axis by adjusting the gradient coils location. The adjacent sectional datasets are overlapped in the overlapped region, and each of the adjacent datasets has a region that is not overlapped. In some embodiments, each of the adjacent sectional datasets includes one or more axial slices (or 2D images) in the overlapped region.

FIG. 3 shows an example method 300 for stitching the sectional datasets to generate a constructed dataset. The sectional datasets obtained by method 200 may be presented (e.g., displayed) by stitching the sectional datasets together using method 300 of FIG. 3. Methods 200 and 300 may be stored in the memory of the imaging system and executed with a controller unit (such as controller unit 25 of FIG. 1).

At 302, the sectional datasets are loaded. The sectional datasets may be loaded into the data processing unit from the memory of the image apparatus of FIG. 1.

At 304, overlapped regions between loaded sectional datasets are determined. The overlapped region may be determined based on the locations of the sectional datasets along the scan axis.

At 306, locations of landmarks within the sectional datasets are determined. The landmark may be an anatomical structure of the image subject. The landmark may be selected based on the location of the overlapped regions of sectional scans along the scan axis. The landmark may also be selected based on the location of the overlapped anatomical section relative to the image subject. In some embodiments, the landmark may be predetermined when loading the sectional datasets. In another example, the landmark may be determined while stitching the sectional datasets. In some embodiments, the landmark is within the subject, and is a part of the subject. The landmark may be fully enclosed within the image subject. In some embodiments, the landmark is nondeformable, so that the landmark in slices acquired from adjacent sectional scans can be registered with minimal error. In some embodiments, the landmark is a bone of the subject. For example, for whole body scan, if the overlapped region of the sectional scans locates at the upper body, the landmark is selected to be the vertebral body; if the overlapped region locates at the lower body, the landmark is selected to be a leg bone.

In some embodiments, locations of the landmark in the slices of the overlapped region may be determined with a trained deep learning neural network. For example, a first slice in a first sectional dataset is selected, and a second slice in a second sectional dataset is selected. The first and the second slices are both in the overlapped region of the first and second sectional datasets. The first and second sectional datasets are acquired from different sectional scans. The first slice and the second slice are within threshold distance from each other along the scan axis, so that the landmark is imaged in both slices. In some embodiments, the threshold distance is less than the slice thickness. In other embodiments, the threshold distance is less than two times of the slice thickness. The landmark may be represented by a subset of data points of the first slice and a subset of pixels of the second slice. Locations of the landmark may be obtained based on a subset of data points in each of the first and second slices. Locations of the landmarks in each of the first and second slices may be determined via the trained neural network, such as the deep learning neural network shown in FIG. 4. Parameters of the trained neural network may be stored in the memory of the imaging system. The trained neural network may output a probability map of landmarks in each slice of the overlapped region. An offset between the datasets may be determined based on the landmark locations.

In some embodiments, a plurality of slices in the overlapped region may be acquired in the adjacent sectional scans. Locations (or coordinates) of the landmark in each of the plurality of slices may be determined via the trained neural network.

At 308, the overlapped sectional datasets are stitched into the constructed dataset by registering (or aligning) the landmarks in adjacent datasets based on an offset.

The offset between the recently loaded sectional datasets and the constructed dataset may be calculated based on location of the landmark in the overlapped region of each dataset. In particular, the offset between locations of the landmark in slices from the overlapped sectional datasets is calculated. In some embodiments, the offset is determined from two slices in the overlapped region of the overlapped sectional datasets. For example, a first slice from a first sectional dataset and a second slice from a second sectional dataset are selected from the overlapped region. The first slice and the second slice are within threshold distance from each other along the scan axis. The offset may be calculated as the difference between the coordinates of the landmark in the first slice and the coordinates of the landmark in the second slice. The offset measures the shift of the landmark in the first slice relative to the second slice. For example, the offset includes the coordinate differences in the axial direction and the transversal direction of the subject.

In another example, the offset is determined based on landmark locations in a plurality of slices from each sectional dataset in the overlapped region. For example, each slice in a first series of slices from the first sectional dataset is paired with a slice in a second series slices from the second sectional dataset based on their respective slice location along the scan axis. For example, slices that are within a threshold distance are paired. The offset may be calculated based on the landmark locations in each pair of slices. Thus, multiple offsets are generated for the multiple pairs of slices. The overall offset between the sectional datasets may be determined based on the multiple offsets. For example, the overall offset may be the median of the multiple offsets. In another example, the overall offset may be the average of the multiple offsets.

In yet another example, the offset may be determined based on locations of a plurality of landmarks. For example, the offset of each landmark may be determined based on locations of each landmark in the slices of adjacent sectional datasets. The overall offset between the sectional datasets may be determined based on the offset of each landmark. For example, the overall offset is the median of the plurality offsets. In another example, the overall offset is the average of the plurality offsets.

In some embodiments, the registration of the landmark is based on data points representing the landmark, but not based on data points other than (not representing) the landmark. In other words, the registration is based on localized information of the slice in the overlapped region, rather than based on global information (or all data points) of the slice.

In some embodiments, stitching the overlapped sectional datasets includes first shifting a first sectional dataset of the overlapped sectional datasets by the offset, then appending the shifted first sectional dataset to a second sectional dataset of the overlapped sectional datasets based the location of the overlapped sectional datasets along the scan axis. No other image processing procedure is performed between shifting the first sectional dataset and appending the shifted first sectional dataset to the second sectional dataset. In some embodiments, shifting the first sectional dataset includes shifting each slice of the first sectional dataset in a plane perpendicular to the scan axis by the offset. In some embodiments, shifting the first dataset includes shifting each data point of the sectional dataset by the offset. FIGS. 6A and 6B show examples of shifting slices by the offset, as well as the constructed dataset generated by stitching two sectional datasets.

The constructed dataset may be displayed and/or stored in the memory of the imaging system. In some embodiments, images in a plane defined by the operator may be generated and displayed based on the constructed dataset. For example, the plane may be a sagittal plane for whole body imaging. The constructed dataset and/or the generated images may be saved in the memory of the imaging system. In some embodiments, the displayed images are directly generated from the constructed data without further image processing, such as filtering, in order to preserve the information from the sectional scans.

Figure 4:
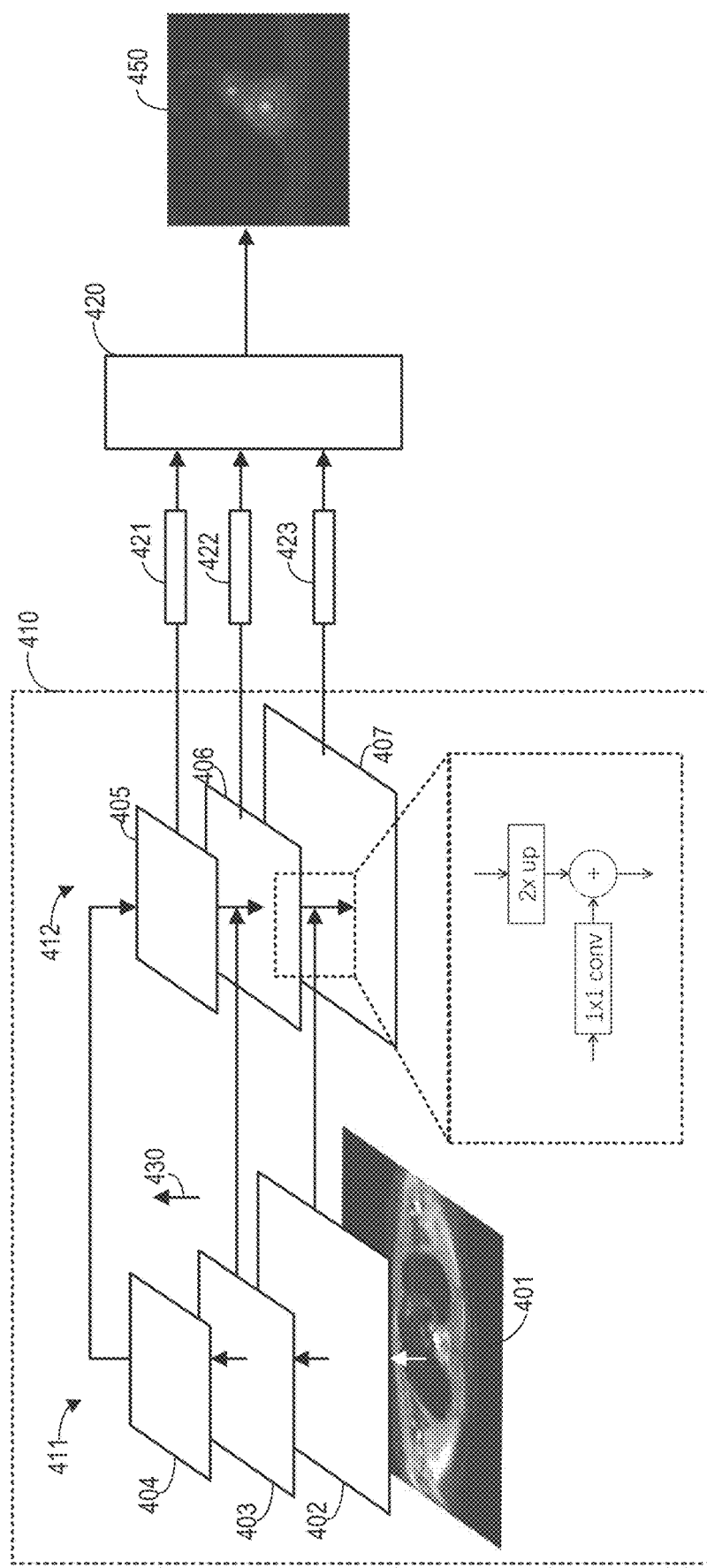
FIG. 4 is a diagram illustrating a neural network for determining location of a landmark in the acquired dataset, according to an exemplary embodiment.

FIG. 4 shows an example deep learning neural network for determining location of the landmark in a slice or 2D image of the sectional dataset. The neural network is trained to detect the selected landmark. In some embodiments, the neural network receives a slice or 2D image 401 and outputs a heatmap 450. The intensity of each pixel in the heatmap 450 indicates the possibility of the pixel belonging to the landmark. The location of the landmark in the slice 401 may be determined based on the heatmap 450. For example, the coordinates of the landmark may be the location of the maximum intensity of the heatmap 450. The neural network may include pyramids 410 for generating reconstructed feature layers.

In some embodiments, the pyramids 410 include a bottom-up pathway 411 and a top-down pathway 412. The bottom-up pathway is a pre-trained backbone network. For example, the bottom-up pathway 411 may be a Residual Net. The input slice 401 is processed based on the trained bottom-up pathway 411 to generate multiscale feature maps 402, 403, and 404 of different levels. Herein, the level increases as indicated by arrow 430. The feature maps are downscaled (that is, sizes of the feature maps are reduced) with increased level. For example, with a scaling step of 2 (that is, the width and the length of the feature map at the higher level is ½ of the width and length of the feature map in the current level), the size of the feature map 402 is ¼ of the size of the input image 401, and the size of the feature map 403 is ¼ of the size of the feature map 402. By reducing the size of the feature map, the semantic value of the feature map increases. Herein, three levels of feature maps are shown in the bottom-up pathway 411.

The first reconstructed feature layer 405 in the top-down pathway 412 is formed by applying a 1×1 convolution filter to the top level of feature map 404. Each lower level reconstructed feature layer is obtained by adding an up-sampled higher level reconstructed feature layer with a corresponding convoluted feature map in the bottom-up pathway 411. For example, the reconstructed feature layer 405 is first up-sampled by two (that is, the size of the reconstructed feature layer increases by 4). The feature map 403 in the bottom-up pathway 411, which is of the same size as the up-sampled reconstructed feature layer 405, is selected and convoluted with a 1×1 convolution filter. Then, the second reconstructed feature layer 406 is obtained by adding the up-sampled reconstructed feature layer 405 with the convoluted feature map 403. Similarly, the reconstructed feature layer 407 of the top-down pathway 412 is obtained by adding the up-sampled reconstructed feature layer 306 with the convoluted feature map 402. Generating the reconstructed feature layer by adding the convoluted feature maps may improve the ability of the neural network to predict location of the object.

Each of the reconstructed feature layers in the top-down pathway 412 is processed by a convolutional layer, and then upsampled at 421, 422, and 423. The upsampled layers are then concatenated together at 420. The concatenated data is processed by multiple convolutional layers to generate the heatmap 450. Each pixel of the heatmap 450 illustrates its possibility to be the landmark. For example, if the intensity of a particular pixel is high, the corresponding pixel in the input slice 401 has a high possibility to be the landmark. The coordinates of the landmark may be the coordinates the pixel with the maximum intensity in the heatmap 450. It should be understood that the layout of the deep learning network as shown in FIG. 4 is for illustration not for limitation. Any appropriate deep learning network may be trained to identity the landmark.

The deep learning neural network of FIG. 4 may be trained using images and corresponding manually labeled landmark locations. For example, regions of a landmark (such as vertebral body) in a plurality of MRI images may be marked manually. The neural network may be trained using the plurality of the MRI images and the corresponding marked regions to determine the parameters of the neural network. The trained parameters of the neural network may then be stored in the memory of the imaging system.

FIG. 5 illustrates an example implementation of the method of FIG. 3, wherein a constructed dataset 515 is generated based on datasets acquired in two sectional datasets. Plot 501 shows the first position of the scanner relative to the subject 16, at which the first sectional dataset 510 of a first section of the subject is acquired in a first sectional scan. Plot 503 shows the second position of the scanner relative to the subject 16, at which the second sectional dataset 512 of the second section of the subject is acquired in a second sectional scan. The second position 503 is reached from the first position 501 by moving table 26 in the direction 540. Plot 502 shows the strength of magnetic field $B_0$ relative to the scan axis. The arrow of the x-axis (scan axis) indicates the scan direction. For example, slices of the subject are acquired in the scan direction. The strength of the magnetic field increases as indicated by the arrow of y-axis. The scan axis aligns with the longitudinal axis of the subject 16. Position of the scan axis is stationary (or fixed) relative to the subject 16. That is, the scan axis moves with the subject when the table 26 is moved from the first position to the second position. The first section of the subject corresponds to a first range from P2 to P4 along the scan axis. The second section of the subject corresponds to a second range from P1 to P3 along the scan axis. The first and second ranges overlap from P2 to P3. Thus, the overlapped section 507 (shaded) of the subject 16 is scanned in both the first and the second sectional scans. The first sectional dataset 510 and second sectional dataset 512 also overlap in an overlapped region, which corresponds to data acquired within the overlapped section 507 of the subject.

Due to the variation in magnetic field strength distribution in the imaging space and the movement of the subject, images of the same cross-section of the subject acquired at different positions may appear different. For example, when the subject is moved through the scanner from the first position 501 to the second position 503, the distribution of magnetic field strength 504 is shifted to the distribution of magnetic field strength 505. As the magnetic field strength is not constant along the scan axis, slices at same position in the scan axis may experience different magnetic field strengths during different sectional scans. Herein, at position 506 along the scan axis, the magnetic field strength 551 of the first image acquired in the first sectional scan is higher than the magnetic field strength 552 of the second image acquired in the second sectional scan. Therefore, the first image and the second image may appear different.

As an example, diffusion-weighted magnetic resonance imaging (DWI) is sensitive to magnetic field change. The same anatomical structure may appear at different locations in the image acquired before and after moving the table. For example, the eye ball may locate at the center of the first image acquired before moving the table, and offset around 5 pixels from the first image in the second image acquired after moving the table. The offset before and after moving the table is unpredictable. Three-dimensional movement of the tissue may introduce additional change in the location and shape of the imaged anatomy between slices acquired in different scans. For these reasons, the shift/translation of a particular anatomical structure (such as a bone) from one slice to another cannot be accurately estimated using conventional registration method, wherein information from the whole slice is utilized. Herein, the offset of the landmark location in slices may be accurately calculated using a subset of data points of each slice.

Each of the first dataset 510 and the second dataset 512 includes a plurality of parallel slices or images along the scan axis. The first image 513 in the first dataset 510 acquired from the first sectional scan, and the second image 514 in the second dataset 512 acquired from the second sectional scan, locate within a threshold from location 506 on the scan axis. The vertebral body (marked by cross "x" in images 513 and 514) is selected as the landmark. An offset 517 of the vertebral body locations in images 513 and image 514 is calculated, for example by subtracting the coordinates of the landmark in one image from the other. A constructed dataset 515 is generated by stitching the first dataset 510 with the second dataset 512 based on the offset 517. The first dataset 510, the second dataset 512, and the constructed dataset 515 are all three-dimensional datasets defined by the longitudinal direction 522, the axial direction 520, and the transversal direction 521. The longitudinal direction aligns with the scan direction. Image 516 showing the anatomy of the subject along the scan direction may be generated based on the constructed dataset 515.

FIG. 6A illustrates shifting or translating a slice (or image) of a dataset based on the location of the landmark in each slice. In some embodiments, the first slice is within the first sectional dataset, and the second slice is within the second sectional dataset. Coordinates of the landmark relative to the slice may be determined via neural network shown in FIG. 4. The coordinate of the landmark in the first slice is (x1, y1), and the coordinate of the landmark in the second slice is (x2, y2). The offset between the first slice and second slice is ($\Delta x$, $\Delta y$), wherein $\Delta x = x2 - x1$ and $\Delta y = y2 - y1$.

Slice (or image) 603 is a slice in the second dataset. Each data point (or pixel) of slice 603 is shifted by $\Delta x$ (shown as 601) in the x axis, and by $\Delta y$ (shown as 602) in the y axis, to obtain the shifted slice 604 (dashed line). For example, coordinate (x, y) of a particular data point in slice 603 is adjusted to a new coordinate (x+$\Delta x$, y+$\Delta y$) in slice 604. Data points in region 605 are deleted, and data points in region 606 may be zero padded.

FIG. 6B shows a constructed dataset 620 generated by stitching adjacent sectional datasets. The first sectional dataset 631 corresponds to range 621 along the scan axis, and the second sectional dataset corresponds to range 622 along the scan axis. Arrow of the scan axis indicates the scan direction. The first and second sectional datasets overlap in overlapped range 623. The first and second sectional datasets each includes multiple slices perpendicular to the scan axis. In some embodiments, each slice in the second sectional dataset that is not overlapped with the first sectional dataset is shifted or translated by the offset to generate shifted dataset 632. The shifted dataset 632 is appended or attached to the first sectional dataset 631 along the scan axis based on the location of the shifted dataset 632 relative to the scan axis.

In another example, the second sectional dataset is shifted and appended to the first sectional dataset that is not overlapped with the second sectional dataset. In yet another example, the constructed dataset may include three sections appended together. The first section is the portion of the first sectional dataset that is not overlapped with the second sectional dataset. The third section is the portion of the second sectional dataset that is not overlapped with the first sectional dataset shifted based on the offset. The second section corresponds to the overlapped range and is between the first section and the second section. The second section may include data generated by combining the overlapped region of the first and the second sectional datasets. The overlapped region of the first and second sectional datasets may be combined based on offset between the first and the second sectional datasets.

FIG. 7A and FIG. 7B show longitudinal images of the subject generated with constructed datasets acquired from adjacent sectional scans. FIGS. 7A and 7B are generated with the same sectional datasets, but the sectional datasets are stitched together differently. The arrow on the scan axis indicates the scan direction. In this example, the scan is performed from anterior to posterior. Pixels correspond to range 710 along the scan axis are based on the first sectional dataset, and pixels correspond to range 711 are based on the second sectional dataset. Line 712 indicates the position where the first sectional dataset and the second sectional dataset meet.

In FIG. 7A, the constructed dataset is stitched based on an offset generated using global information of slices in the overlapped region. As information of the whole slices (that is, all data pointes of the slice) is considered when calculating the offset between the two slices, the stitching error may vary at localized spots. For example, the stitching error is not constant along line 712. The spine of the subject appears broken at position 701 due to large stitching error. The offset error at position 702 is lower, therefore no discontinuity presents at 702 and the rib cage appears smooth. However, without knowledge of the distribution of the stitching error, the operator may misdiagnose and consider that the subject's spine is broken.

In FIG. 7B, the constructed dataset is obtained based on method 300 of FIG. 3. The sectional datasets are stitched together based on localized information of the slices (that is, a subset of data points of the slice). In particular, the offset is generated using the landmark locations in the slices of the overlapped region. The landmark is selected to be the vertebral core. Since the offset is generated based on localized information in the slice (that is, location of the vertebral core determined based on a subset of data points of the slice), the stitching error is the lowest at the landmark, such as position 703 of the vertebral core. Therefore, the discontinuity at 701 of FIG. 7A is absent in FIG. 7B. The stitching error at position 704 is large, which introduces discontinuity of the rib cage. However, since it is well known that the rib cage may appear broken due to respiratory motion, the operator can predict that the discontinuity at 704 is an artifact. In this way, misdiagnosis due to stitching error may be avoided.

The technical effect of calculating the offset between sectional datasets based location of the landmark is that the stitching error is the minimal at the landmark location, and misdiagnosis caused by stitching error may be reduced. The technical effect of selecting a landmark that is a part of the subject is that the landmark appears continuous in the image generated from the constructed dataset. The technical effect of translating each data point in the sectional datasets by the offset to construct the constructed dataset and directly displaying the constructed data is that the information in the sectional dataset may be preserved.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for medical imaging, comprising:
performing a first sectional scan on a first anatomical section of an image subject to obtain a first sectional dataset;
performing a second sectional scan on a second anatomical section of the image subject to obtain a second sectional dataset;
determining, with a trained deep learning network, a first location of a landmark in the first sectional dataset and a second location of the landmark in the second sectional dataset; and
stitching together the first sectional dataset and the second sectional dataset based on an offset between the first location and the second location.

2. The method of claim 1, wherein the first sectional dataset and the second sectional dataset are three-dimensional datasets partially overlapped along a scan axis of the image subject, the first location of the landmark is coordinates of the landmark within a first plane perpendicular to the scan axis, and the second location of the landmark is coordinates of the landmark within a second plane perpendicular to the scan axis.

3. The method of claim 2, wherein the first sectional dataset and the second sectional dataset comprise a plurality of parallel axial slices perpendicular to the scan axis.

4. The method of claim 1, wherein the trained deep learning network includes a bottom-up pathway and a top-down pathway.

5. The method of claim 1, wherein the first sectional dataset and the second sectional dataset are acquired via magnetic resonance imaging.

6. The method of claim 1, wherein stitching the first sectional dataset and the second sectional dataset based on the offset between the first location and the second location includes stitching the first sectional dataset and the second sectional dataset by translating the second sectional dataset by the offset, and stitching the translated second sectional dataset to the first sectional dataset based on positions of the first sectional dataset and the second sectional dataset along a scan axis.

7. The method of claim 1, wherein the landmark is within the image subject and in an overlapped anatomical section between the first anatomical section and the second anatomical section of the image subject, and the landmark is selected based on a position of the overlapped anatomical section relative to the image subject.

8. The method of claim 1, wherein the landmark is a vertebral body when the first anatomical section of the image subject includes an upper body of the image subject, and the landmark is a leg bone when the second anatomical section of the image subject includes a lower body of the image subject.

9. The method of claim 1, further comprising acquiring a third sectional dataset of a third anatomical section of the image subject; selecting a second landmark; and
stitching the third sectional dataset to the stitched first sectional dataset and the second sectional dataset based on a third location of the second landmark in the second sectional dataset and a fourth location of the second landmark in the third sectional dataset.

10. An imaging apparatus, comprising:
a scanner configured to scan an image subject;
a table for placing the image subject, the table movable relative to the scanner;
a memory storing a trained deep learning network;
a controller coupled to the scanner, the table, and the memory and configured to:
instruct the scanner to perform a first sectional scan on a first anatomical section of the image subject to acquire a first sectional dataset;
move the table relative to the scanner;
instruct the scanner to perform a second sectional scan on a second anatomical section of the image subject to acquire a second sectional dataset;
determine a first location of a landmark in the first sectional dataset and a second location of the landmark in the second sectional dataset with the trained deep learning network;

determine an offset between the first location and the second location; and stitch together the first sectional dataset and the second sectional dataset by translating the second sectional dataset by the offset, and stitching the translated second sectional dataset to the first sectional dataset based on positions of the first sectional dataset and the second sectional dataset along a scan axis.

11. The imaging apparatus of claim 10, wherein the trained deep learning network outputs heatmaps of the landmark in the first sectional dataset and the second dataset.

12. The imaging apparatus of claim 11, wherein the first location and the second location of the landmark correspond to locations of a maximum value in the heatmaps.

13. The imaging apparatus of claim 10, wherein the controller is further configured to calculate an offset based on the first location of the landmark in the first sectional dataset and the second location of the landmark in the second sectional dataset, and wherein stitching the first sectional dataset and the second sectional dataset based on the first location of the landmark and the second location of the landmark includes stitching the first sectional dataset and the second sectional dataset by aligning the landmark in the first sectional dataset and the landmark in the second sectional dataset based on the offset.

14. The imaging apparatus of claim 10, wherein the landmark is selected by an operator based on a location of an overlapped region between the first sectional dataset and the second sectional dataset along a scan axis.

15. A non-transitory computer-readable medium comprising instructions that, when executed, cause a processor to:

perform a first sectional scan on a first anatomical section of an image subject to obtain a first sectional dataset;

perform a second sectional scan on a second anatomical section of the image subject to obtain a second sectional dataset;

determine, with a trained deep learning network, a first location of a landmark in the first sectional dataset and a second location of the landmark in the second sectional dataset; and stitch together the first sectional dataset and the second sectional dataset based on an offset between the first location and the second location.

16. The computer-readable medium of claim 15, further comprising instructions, when executed, cause the processor to construct a constructed image based on the stitched first sectional dataset and the second sectional dataset.

17. The computer-readable medium of claim 15, further comprising instructions, when executed, cause the processor to select a first image in the first sectional dataset, and select a second image in the second sectional dataset, wherein the landmark is within both the first image and the second image, and wherein the first location of the landmark in the first sectional dataset includes the first location of the landmark in the first image, the second location of the landmark in the second sectional dataset includes the second location of the landmark in the second image.

18. The computer-readable medium of claim 15, wherein the first location of the landmark in the first sectional dataset and the second location of the landmark in the second sectional dataset are determined based on heatmaps outputted by the trained deep learning network, the heatmaps representing a probability of a pixel belonging to the landmark.

19. The computer-readable medium of claim 15, wherein the trained deep learning network is determined based on a plurality of images and manually labeled locations of the landmark in the plurality of images.

* * * * *